United States Patent [19]

Michurov et al.

[11] 4,122,289
[45] Oct. 24, 1978

[54] METHOD FOR PREPARING 2,6-DITERT.BUTYLPHENOL

[76] Inventors: Jury Ivanovich Michurov, prospekt Lenina, 13, kv. 4, Bashkirskaya ASSR, Sterlitamak; Vladimir Avgustovich Yanshevsky, ulitsa Kommunisticheskaya, 42, kv. 12; Rufina Alexandrovna Filippova, prospekt Uspenskogo, 3, kv. 19, both of Novokuibyshevsk; Yakov Abramovich Gurvich, Sretensky bulvar, 8, kv. 61, Moscow; Igor Jurievich Logutov, ulitsa Druzhby, 47, kv. 50; Sofya Alexandrovna Egoricheva, ulitsa Nagumanova, 56-a, kv. 23, both of Bashkirskaya ASSR, Sterlitamak; Izrail Markovich Belgorodsky, ulitsa Karla Marxa, 50, kv. 25; Sergei Gerasimovich Vyborov, ulitsa Karla Marxa, 66, kv. 24, both of Tolyatti, all of U.S.S.R.

[21] Appl. No.: 822,376

[22] Filed: Aug. 5, 1977

[30] Foreign Application Priority Data

Aug. 11, 1976 [SU] U.S.S.R. .................... 2409070

[51] Int. Cl.$^2$ ............................................ C07C 39/06
[52] U.S. Cl. .................................................. 568/789
[58] Field of Search ........................ 260/624 C, 624 R

[56] References Cited

U.S. PATENT DOCUMENTS

| | | | |
|---|---|---|---|
| 2,831,898 | 4/1958 | Ecke et al. | 260/624 C |
| 3,032,595 | 5/1962 | Neuworth | 260/624 C |
| 3,048,563 | 8/1962 | Seydel et al. | 260/624 C |

FOREIGN PATENT DOCUMENTS

| | | | |
|---|---|---|---|
| 1,809,555 | 10/1969 | Fed. Rep. of Germany | 260/624 C |
| 1,062,298 | 4/1967 | United Kingdom | 260/624 C |
| 236,484 | 11/1970 | U.S.S.R. | 260/624 C |

Primary Examiner—James O. Thomas, Jr.
Assistant Examiner—Werren B. Lone
Attorney, Agent, or Firm—Haseltine, Lake & Waters

[57] ABSTRACT

A method for preparing 2,6-ditert.butylphenol which comprises alkylation of phenol in the presence of mono-tert.-butylphenol and a catalyst, viz. aluminium dissolved in phenol with gradually lowering the process temperature from 120° to 50° C and reducing the concentration of isobutylene in the mixture of isomeric butenes from 80 to 1.5 mol.%, followed by isolation of the desired product.

The method according to the present invention makes it possible to achieve a high degree of conversion of isobutylene without impairing quality of the desired product. The amount of by-products formed in the process is 2-3 times as less as in the prior art methods.

2 Claims, 1 Drawing Figure

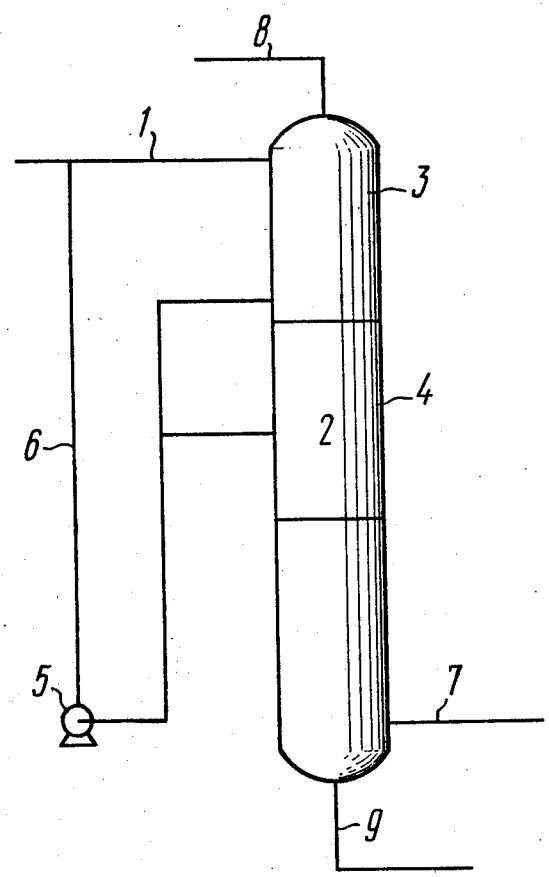

METHOD FOR PREPARING 2,6-DITERT.BUTYLPHENOL

FIELD OF APPLICATION OF THE INVENTION

The present invention relates to petrochemical and chemical industries and, more specifically, to methods for preparing 2,6-ditert.butylphenol which is useful in the production of stabilizing agents for polymeric materials.

BACKGROUND OF THE INVENTION

Known in the art is a method for preparing 2,6-ditert.-butylphenol by way of alkylation of phenol with pure isobutylene in the presence of a catalyst, i.e. aluminium dissolved in phenol (cf. FRG Pat. No. 1,137,444; Stroh R, Seydel R, Hohn W, Angew. Chem. 69, 6991, 1957).

In this method ortho-tert.butylphenol and 65 to 70 mol.% of 2.6-ditert.butylphenol are obtained. This method has a disadvantage residing in a high cost of the employed pure isobutylene which is recovered from isobutylene-containing hydrocarbons by special sophisticated methods.

Known in the art is alkylation of phenol with normal butenes at a temperature of from 140° to 240° C. in the presence of a catalyst, i.e. aluminium dissolved in phenol. At the temperature of 150° C. the yield of 2-sec.-butylphenol is 27.5 mol.% (cf. FRG Pat. No. 2,333,745).

Further known is a method for preparing 2,6-ditert.butyl phenol in a mixture with 2-tert.butylphenol. Alkylation of phenol is effected with a mixture of isomeric butenes containing about 50 molar % of isobutylene in the presence of a catalyst, i.e. aluminium dissolved in phenol, and at a temperature within the range of from 70 to 250° C., preferably from 90° to 130° C.

This method has a disadvantage residing in the formation, in the process, of a by-product, i.e. 2-sec.butylphenol in a conentration which depends on the content of isobutylene in the starting mixture of isomeric butenes.

In Table 1 data are shown which demonstrate selectivity of the alkylation process depending on the starting and final content of isobutylene in the mixture of isomeric butenes.

Table 1

| Test No. | Temp. °C | Isobutylene concentration in the mixture of isomeric butenes, mol.% | | Concentration of the final products, mol.% | |
|---|---|---|---|---|---|
| | | Starting | Final | 2,6-ditert. butylphenol | 2-sec.butyl- phenol |
| 1 | 110 | 45.4 | 20.4 | 65.5 | 0.7 |
| 2 | 110 | 45.4 | 4.1 | 66.2 | 3.2 |

As it is seen from the Table, the higher conversion of isobutylene, the greater is the amount of the by-product, i.e. 2-sec.butylphenol. The presence of said by-product results in that isobutylene contained in the mixture of isomeric butenes is used only partially which is economically inefficient. It is impossible to totally recover isobutylene at a high selectivity of the process. After the alkylation process normal butenes containing 20.4 and mol.% of isobutylene remain which do not find any wide application.

BRIEF SUMMARY OF THE INVENTION

It is an object of the present invention to provide a high conversion of isobutylene contained in a mixture of isomeric butenes simultaneously with a reduced yield of by-products - sec.butylphenols.

This object is accomplished by that in a method for preparing 2,6-ditert.butylphenol by way of alkylation of phenol with a mixture of isomeric butenes in the presence of a catalyst, i.e. aluminium dissolved in phenol upon heating, in accordance with the present invention said alkylation of phenol is conducted in the presence of monotert.butylphenol while progressively lowering the process temperature from 120° to 50° C. with decreasing concentration os isobutylene in a mixture of isomeric butenes from 80 to 1.5 mol.%.

It is desirable to perform alkylation of phenol in the presence of 20 to 50 mol.% of monotert, butylphenol.

DETAILED DESCRIPTION OF THE INVENTION

The method according to the present invention is performed in the following manner.

In the alkylation of phenol with a mixture of isomeric butenes, the rate of formation of 2-sec.butylphenol depends on the degree of alkylation of phenol with isobutylene. Upon increasing of the degree of alkylation of phenol there occurs a simultaneous decrease of the of rate alkylation with both isobutylene and normal butenes. However, decrease of the rate of alkylation of phenol with normal butenes occurs substantially faster as it is seen from Table 2 hereinbelow.

Table 2

| Phenol concentration in the mixture with monotert. butylphenol, mol. percent | Relative decrease of the rate of alkylation of phenol | |
|---|---|---|
| | with isobutylene | with normal butylenes |
| 100 | 1.0 | 1.0 |
| 90 | 0.93 | 0.74 |
| 80 | 0.86 | 0.43 |
| 70 | 0.78 | 0.30 |
| 60 | 0.70 | 0.21 |
| 50 | 0.63 | 0.12 |

As it is seen from Table 2, to increase the degree of alkylation of phenol, it is necessary to add monotert.-butylphenol in such an amount that the concentration of the starting phenol would not exceed 80 mol.%. It is preferable to perform alkylation of phenol in the presence of 20 to 50 mol.% of monotert.butylphenol.

Relative rate of alkylation of phenol with isobutylene and normal butenes is strongly influenced by temperature of the alkylation process. With increasing reaction temperature the ratio of alkylation rate constants phenol with normal butenes and isobutylene is increased and, hence, the content of 2-sec.butylphenol in the reaction products is increased. The effect of temperature on the ratio between constants of speed of the alkylation of phenol with normal butenes and isobutylene is shown in Table 3 hereinbelow.

Table 3

| Temperature, °C | Ratio between alkylation rate constants of phenol with normal butenes and isobutylene |
|---|---|
| 90 | 1,170 |
| 100 | 580 |
| 110 | 270 |

The highest amount of 2-sec.butylphenol is formed at low concentrations (below 5 mol.%) of isobutylene in the mixture of isomeric butenes, wherefore in this case the temperature of the alkylation reaction should be maximally lowered. In order to ensure that the reaction time would not be too long at a higher concentration of isobutylene in the mixture of isomeric butenes, the temperature should be elevated. Taking into consideration the fact that the maximum yield of 2,6-ditert.butylphenol is observed at a temperature of not more than 120° C, it is undesirable to start the alkylation process at a higher temperature.

To prepare 2,6-ditert.butylphenol by the method according to the present invention, a catalyst of the alkylation process, i.e. aluminium dissolved in phenol, is prepared by any conventional method.

Into the starting molten phenol containing the above-mentioned catalyst, monotertbutylphenol is added and this mixture is fed via a line 1 into the upper part of a reactor 2. Concentration of phenol in the mixture should not exceed 80 mol.%. The reactor is divided into three zones in the case where the starting phenol is fed into the reactor at a concentration above 80 mol.%. Monotert.butylphenol, as it is formed during the alkylation process, from the zone 3 or 4 is pumped by a pump 5 via a line 6 to mixing with the starting phenol so that the concentration of phenol at the inlet of the reactor would not exceed 80 mol.%. A mixture of isomeric butenes is fed via a line 7 of the reactor 2. Upon reduction of the concentration of isobutylene from 80 to 1.5 mol.% in the mixture of isomeric butenes, temperature in the reactor is varied from 120° C. in the lower part of the reactor to 50° C. in the upper part of the reactor. A mixture of normal butenes containing 2 to 5 mol.% of isobutylene is discharged from the upper part of the reactor via a line 8. From the lower part of the reactor a mixture of tert.butylphenols is discharged via a line 9, from which mixture 2,6-ditert.butylphenol is separated by rectification after destruction of the catalyst by water.

Due to varied process conditions a high conversion of isobutylene is ensured as compared to the prior art methods for preparing 2,6-ditert,butylphenol, without, however, impairing quality of the final product. Furthermore, the amount of formed by-products is 2-3 times as less as in the prior art methods for the preparation of 2,6-ditert.butylphenol. Normal butenes remaining after alkylation of phenol and containing below 5 mol.% of isobutylene find an extensive commercial use for the production of divinyl, methylethylketone and other products.

For a better understanding of the present invention some specific Examples illustrating the method for preparing 2,6-ditert.butylphenol are given hereinbelow.

EXAMPLE 1

In 40 g of phenol there is dissolved 0.7 g of metallic aluminium at the temperature of 160° C.; the solution is cooled to the temperature of 100° C. and added with 62 g of a fraction of 2-tertbutylphenol having the following composition, mol.%: 2-tertbutylphenol 96.8; phenol 2.4; 2,6-ditert.butylphenol 0.9. The resulting mixture is cooled to the temperature of 50° C. and fed into the upper part of a counter-current type reactor. Into the lower part of the reactor there are fed 155 g of a mixture of isomeric butenes containing 78 mol.% of isobutylene. As the concentration of isobutylene in the mixture is decreased in the mixture of isomeric butenes, the temperature in the reactor is decreased from 120° C. in the lower part of the reactor to 50° C. in the upper part of the reactor. From the upper part of the reactor there is discharged a mixture of isomeric butenes containing 2 mol.% of isobutylene. From the bottom part of the reactor there are discharged 225 g of a mixture of alkylaphenols having the following composition, molar percent: tertbutyl ether 0.3; phenol 0.4; 2-tert.butylphenol 23.1; 2-sec.butylphenol 0.2; 4-tert.butylphenol 0.2; 2,6-ditert.butylphenol 61.5; 2,4-ditert.butylphenol 6.0; 2,4,6-tritert.tritert.butylphenol 8.3. After destruction of the catalist with water, 145 g of 2,6-ditertbutylphenol are recovered from the mixture of the alkylaphenols by rectification. The yield is equal to 61 mol.%.

At the depth of recovery of isobutylene of down to 2%, concentration of 2-sec.butylphenol is 0.3 mol.% relative to 2,6-ditert.butylphenol.

EXAMPLE 2

In 64.3 g of phenol there is dissolved 1.1 g of aluminium at the temperature of 160° C.; the solution is cooled to the temperature of 100° C. and added with 26.7 g of 2-tert.butylphenol. The mixture is cooled to the temperature of 50° C. and delivered into the top section of a counter-current type reactor. Into the bottom section of the reactor there are fed 250 g of a mixture of isomeric butenes containing 50% by weight of isobutylene. As the concentration of isobutylene in the mixture of isomeric butenes is decreased, the temperature in the reactor is also decreased from 120° C. in the bottom part to 50° C. in the top part of the reactor. From said top part of the reactor a mixture of isomeric butenes is discharged containing 1.7 mol.% of isobutylene. From the bottom part of the reactor 234 g of a mixture of alkylphenols are discharged which mixture has the following composition, molar percent: tert.butyl ether 0.4; phenol 0.5; 2-tert.butylphenol 21.1; 4-tertbutylphenol 0.2; 2-sec.butylphenol 0.2; 2,6-ditert.butylphenol 65.0; 2.4-ditert.butylphenol 5.0; 2,4,6-tritert.butylphenol 7.6. After breaking of the catalyst with water, 159 g of 2.6-ditert.butylphenol are recovered from the mixture of alkylphenols by rectification. The yield is 65 mol.%.

EXAMPLE 3

62 g of phenol are heated to the temperature of 100° C., added, in a current of dry nitrogen, with 5.6 ml of triisobutylaluminium and 43.5 g of 2-tert.butylphenol. The mixture is cooled to the temperature of 50° C. and supplied into the top part of a counter-current ype reactor. Into the bottom part of the reactor there are fed 255 g of a mixture of isomeric butenes containing 45 mol.% of isobutylene. The alkylation reaction is further conduced under the conditions described in the foregoing Example 1.

From the top part of the reactor a mixture of isomeric butenes is discharged containing 1.5 mol.% of isobutylene. From the bottom part there is discharged a mixture, in the amount of 220 g, of alkylphenols having the following composition, molar percent; tert.butyl ether 0.2; phenol 0.8; 2-tert.butylphenol 23.6; 4-tert.butylphenol 0.4; 2-sec.butylphenol 0.2; 2,6-ditert.butylphenol 61.8; 2,4-ditert.butylphenol 5.2; 2,4,6-tritert.butylphenol 7.8. After destruction of the catalyst with water, 142 g of 2,6-ditert, butylphenol are recovered from the mixture of alkylphenols by rectification. The yield is 65 mol.%.

EXAMPLE 4

To 53 g of phenol there are added 55 g of 4-tert.butylphenol. The mixture is heated to the temperature of 100° C. and added, in a current of dry nitrogen, with 5.0 g of triisobutyl aluminium; then the mixture is cooled to the temperature of 50° C. and fed into the top part of a counter-current type reactor. Into the bottom part of the reactor there are fed 286 g of a mixture of isomeric butenes containing 45% by weight of isobutylene. The alkylation reaction is further conducted under the conditions described in the foregoing Example 1.

From the top part of the reactor a mixture of isomeric butenes is discharged which mixture contains 2.6 mol.% of isobutylene. From the bottom part of the reactor there are discharged 235 g of a mixture of alkylphenols having the following composition, molar percent: tert. butyl ether 0.6; phenol 0.4; 2-tert.butylphenol 20.5; 2-sec.butylphenol 0.2; 4-tertbutylphenol 19.2; 2,6-ditert. butylphenol 28.0; 2.4-ditert.butylphenol 15.1; 2,4,6-tritert.butylphenol 16.0.

After destruction of the catalyst with water, 153 g of 2,6-ditert.butylphenol are recovered from the mixture of alkyl phenols by rectification. The yield is 65 mol.%.

What is claimed is:

1. A method for preparing 2,6-ditert.butylphenol which comprises alkylating phenol with a mixture of isomeric butenes in the presence of monotert.-butylphenol and as catalyst, aluminum dissolved in phenol, the concentration of aluminum being 0.1-5% by weight of the phenol with gradual lowering of the temperature from 120° to 50° C., with concurrent reduction of the concentration of isobutylene in the mixture of isomeric butenes from 80 to 1.5 mol.%, followed by isolating the desired product.

2. A method as claimed in claim 1, wherein said alkylation of phenol is carried out in the presence of monotert.-butylphenol in an amount ranging from 20 to 50 mol.%.